US00PP28845P3

(12) United States Plant Patent
Klemm et al.

(10) Patent No.: US PP28,845 P3
(45) Date of Patent: Jan. 2, 2018

(54) ***PELARGONIUM* PLANT NAMED 'KLEPS15378'**

(50) Latin Name: *Pelargonium grandiflorum*
Varietal Denomination: KLEPS15378

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 76 days.

(21) Appl. No.: 14/998,948

(22) Filed: Mar. 9, 2016

(65) Prior Publication Data

US 2017/0265359 P1 Sep. 14, 2017

(51) Int. Cl.
*A01H 5/02* (2006.01)

(52) U.S. Cl.
USPC ..... Plt./324

(58) Field of Classification Search
USPC ..... Plt./324
See application file for complete search history.

(56) References Cited

PUBLICATIONS

UPOV hit on a *Pelargonium* plant named 'KLEPS 15378', CH PBR 16-3072, application date Jul. 31, 2016.*
UPOV hit on a *Pelargonium* plant named 'KLEPS15378', QZ PBR 20161688, application date Jul. 4, 2016.*

* cited by examiner

*Primary Examiner* — Anne M Grunberg
(74) *Attorney, Agent, or Firm* — Barbara Campbell; James M. Weatherly; Cochran Freund & Young, LLC

(57) ABSTRACT

A new *pelargonium* plant particularly distinguished by dark salmon-red flowers with dark-red eyes, and an upright, round, and bushy habit, is disclosed.

1 Drawing Sheet

Genus and species: *Pelargonium grandiflorum.*
Variety denomination: 'KLEPS15378'.

BACKGROUND OF THE NEW PLANT

The present invention comprises a new and distinct variety of *pelargonium*, botanically known as *Pelargonium grandiflorum* and hereinafter referred to by the variety name 'KLEPS15378'. 'KLEPS15378' originated from a cross-combination in July 2010 in Stuttgart, Germany between the proprietary female *pelargonium* variety 'PS-2009-0001' (unpatented) and the proprietary male *pelargonium* variety 'PSH-2009-C-Bright Red' (unpatented).

Seeds from the cross-combination in Stuttgart, Germany were obtained. The seeds were sown and plants were grown for evaluation. A single plant was selected in June 2011 and subsequently named 'KLEPS15378'. In August 2011 'KLEPS15378' was first vegetatively propagated by vegetative cuttings from stems and braches. 'KLEPS15378' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Dark salmon-red flowers with dark-red eyes; and
2. An upright, round, and bushy habit.

DESCRIPTION OF THE PHOTOGRAPH

This new *pelargonium* plant is illustrated by the accompanying photograph which shows an overall view of the plant. The photograph is of an approximately ten-week-old plant grown in Stuttgart, Germany under greenhouse conditions in April 2014. The colors shown are as true as can be reasonably obtained by conventional photographic procedures.

DESCRIPTION OF THE NEW VARIETY

The following detailed descriptions set forth the distinctive characteristics of 'KLEPS15378'. The data which define these characteristics were collected from asexual reproductions carried out in Stuttgart, Germany. Data was collected on plants grown five-months after planting in Stuttgart, Germany under greenhouse conditions in July 2015. Color references are to The R.H.S. Colour Chart of The Royal Horticultural Society of London (R.H.S.), 5$^{th}$ edition (2007).

Classification:
- *Family.*—Geraniaceae.
- *Botanical.*—*Pelargonium grandiflorum.*
- *Common.*—*Pelargonium.*
- *Designation.*—'KLEPS15378'.

Parentage:
- *Female parent.*—The proprietary female *pelargonium* variety 'PS-2009-0001' (unpatented).
- *Male parent.*—The proprietary male *pelargonium* variety 'PSH-2009-C-Bright Red' (unpatented).

Plant:
- *Form.*—Bushy and round.
- *Habit.*—Upright.
- *Height.*—23.0 cm.
- *Width.*—24.0 cm.
- *Natural flowering season.*—Spring to autumn.
- *Propagation type.*—Vegetative cuttings.

*Time to produce a finished flowering plant.*—4 to 5 months.
*Time to initiate and develop roots.*—28 days.
*Root description.*—RHS27D and fine.

Stems:
*Quantity of stems per plant.*—5 to 6.
*Color.*—RHS 137A.
*Surface texture.*—Moderately pubescent.
*Stem form.*—Round.
*Diameter.*—0.5 cm.
*Length.*—4.0 cm to 6.0 cm.
*Internode length.*—1.0 cm to 1.3 cm.
*Anthocyanin.*—Absent.

Leaves:
*Arrangement.*—Alternate.
*Shape.*—Cordate.
*Apex.*—Acute.
*Base.*—Open.
*Margin.*—Crenate.
*Surface texture.*—Upper surface: Smooth to sparsely pubescent. Lower surface: Smooth.
*Length.*—4.0 cm to 5.0 cm.
*Width.*—4.0 cm to 5.0 cm.
*Color.*—Upper surface: RHS 137B. Lower surface: RHS 137C.
*Petiole.*—Length: 4.0 cm to 7.0 cm. Diameter: 0.2 cm. Color: RHS 137C. Strength: Medium.
*Venation pattern.*—Palmate.
*Venation color.*—Upper surface: RHS 137B. Lower surface: RHS 137D.

Inflorescence:
*Lastingness of flowers on the plant.*—7 to 10 days.
*Umbels.*—Quantity of umbels per plant: 5 to 6. Length: 4.0 cm. Diameter: 5.0 cm.
*Individual florets of the umbel.*—Quantity of florets per umbel: 3 to 6. Depth: 2.3 cm. Diameter: 4.0 cm.
*Fragrance.*—Absent.

Flower buds:
*Cluster shape.*—Round.
*Cluster size.*—Length: 1.5 cm. Width: 1.5 cm.
*Surface texture.*—Moderately pubescent.
*Bud.*—Height: 0.6 cm to 0.8 cm. Width: 0.5 cm. Shape: Elliptic. Apex: Acute. Base: Obtuse. Margin: Entire. Color: RHS 137B.

Petals:
*Quantity per flower.*—5 to 7.
*Shape.*—Drop-shaped.
*Apex.*—Round.
*Base.*—Obtuse.
*Margin.*—Entire.
*Length.*—2.5 cm.
*Width.*—1.0 cm to 2.0 cm.
*Surface texture.*—Upper surface: Smooth. Lower surface: Smooth.
*Color of lobes.*—Upper lobes: Upper surface: RHS 53B (Red) with RHS N77A (Purple) centers. Lower surface: RHS 53B (Red) with RHS N77A (Purple) centers. Lower lobes: Upper surface: RHS 53C (Red) with RHS N77A (Purple) centers. Lower surface: RHS 53C (Red) with RHS 59B (Red-purple) centers.

Petaloids: Absent.

Sepals:
*Number per flower.*—5.
*Shape.*—V-shaped.
*Apex.*—Cuspidate.
*Base.*—Obtuse.
*Margin.*—Entire.
*Surface texture.*—Upper surface: Smooth. Lower surface: Moderately pubescent.
*Color.*—Upper surface: RHS 137D. Lower surface: RHS 137C.
*Length.*—1.2 cm.
*Width.*—0.6 cm.

Pedicel:
*Length.*—2.0 cm.
*Diameter.*—0.1 cm.
*Color.*—RHS 137B.
*Surface texture.*—Moderately pubescent.
*Strength.*—Medium.

Peduncle:
*Length.*—4.0 cm to 6.0 cm.
*Diameter.*—0.2 cm.
*Color.*—RHS 137A.
*Surface texture.*—Moderately pubescent.
*Strength.*—Medium.

Reproductive organs:
*Stamens.*—Quantity of stamens per flower: Greater than 5. Anther length: 0.2 cm. Filament length: 1.0 cm. Filament color: RHS 53C. Pollen amount: Moderate. Pollen color: RHS 59D.
*Pistils.*—Number: 1. Stigma color: RHS 59A. Style length: 1.2 cm. Style color: RHS 53A. Ovary arrangement: Central. Ovary color: RHS 138D. Ovary diameter: 0.1 cm. Ovary length: 0.15 cm.

Fruit and seed set: None observed.

Disease and pest/insect resistance: None observed.

COMPARISON WITH PARENTAL LINES AND KNOWN VARIETY

'KLEPS15378' is distinguished from its parents as described in Table 1:

TABLE 1

Comparison with Parental Lines

| Characteristic | 'KLEPS15378' | Female parent 'PS-2009-0001' | Male Parent 'PSH-2009-C-Bright Red' |
|---|---|---|---|
| Flower size | Medium | Small | Larger than 'KLEPS15378' |
| Flower color | Dark salmon-red with dark-red eyes | Purple-red | Bright red with dark-red eyes |

'KLEPS15378' can be compared to the commercial variety 'Camred' (U.S. Plant Pat. No. 20,427), also commercially known as CANDY FLOWERS 'Bright Red'. Differences between the two varieties are described in Table 2:

TABLE 2

Comparison with Similar Variety

| Characteristic | 'KLEP515378' | Commercial line 'Camred' |
|---|---|---|
| Flower color | Dark salmon-red with dark-red eyes | Bright red |

We claim:

1. A new and distinct variety of *pelargonium* plant named 'KLEPS15378' as illustrated and described herein.

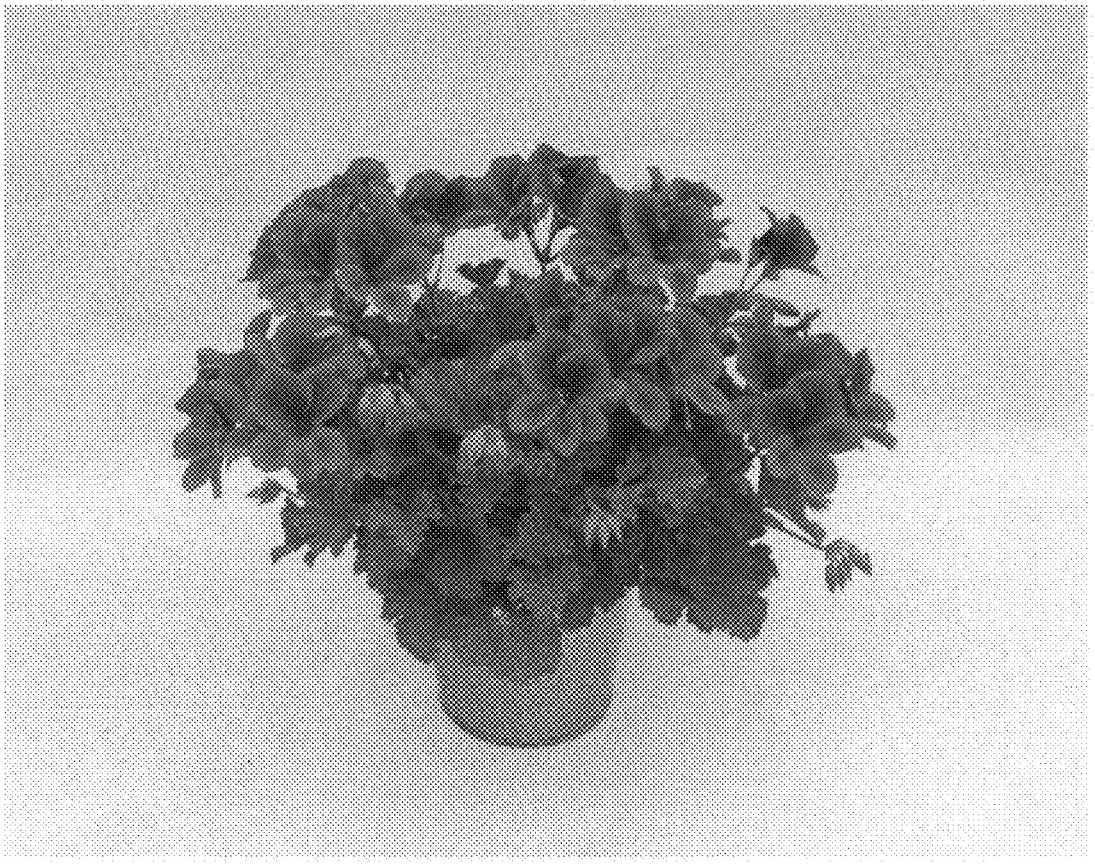

* * * * *